US007419535B2

(12) United States Patent
Malle

(10) Patent No.: US 7,419,535 B2
(45) Date of Patent: Sep. 2, 2008

(54) DEVICE FOR BLOWING A FLOW OF PERFUMED AIR AND INSTALLATION COMPRISING SEVERAL DEVICES

(75) Inventor: Frédéric Malle, Paris (FR)

(73) Assignee: Frederic Malle Consultants, Paris (FR)

( * ) Notice: Subject to any disclaimer, the term of this patent is extended or adjusted under 35 U.S.C. 154(b) by 447 days.

(21) Appl. No.: 11/033,392

(22) Filed: Jan. 12, 2005

(65) Prior Publication Data

US 2005/0212151 A1 Sep. 29, 2005

(30) Foreign Application Priority Data

Jan. 15, 2004 (FR) .................................. 04 50088

(51) Int. Cl.
*B01F 3/04* (2006.01)
*B01D 50/00* (2006.01)
(52) U.S. Cl. .............................. 96/222; 261/26; 261/30; 261/DIG. 88; 422/124
(58) Field of Classification Search ................... 261/26, 261/30, DIG. 88; 422/4, 124; 96/222
See application file for complete search history.

(56) References Cited

U.S. PATENT DOCUMENTS 5,069,876 A * 12/1991 Oshinsky ........................ 422/4
6,371,451 B1 * 4/2002 Choi ............................ 261/26

* cited by examiner

*Primary Examiner*—Robert A Hopkins
(74) *Attorney, Agent, or Firm*—Young & Thompson

(57) ABSTRACT

A device for blowing (16) an air flow (12) filled with a fragrant substance, particularly a perfume to be tested, includes a dilution system (18), in which the air flow (12) circulates at a generally constant flow rate, which emerges in a blower nozzle (22) and into which the substance is injected, a reservoir (32) in which the substance is stored in liquid form and a system for sampling (34) a predetermined quantity of the substance, from the reservoir (32) and continuously, via a sampling gas, which emerges into the dilution system (18), characterized in that the sampling gas is air which is aspirated from a volume of ambient air. The invention also proposes an installation (10) having several blower devices (16) aligned longitudinally.

19 Claims, 5 Drawing Sheets

DEVICE FOR BLOWING A FLOW OF PERFUMED AIR AND INSTALLATION COMPRISING SEVERAL DEVICES

The invention concerns a device for mixing a certain quantity of a perfume in an air flow, and for blowing the air flow filled with this quantity of perfume towards the face of a person, particularly of a customer wanting to test that perfume in a shop in which the device is installed.

The invention proposes more particularly a device for blowing an air flow filled with a fragrant substance, particularly a perfume to be tested, of the type comprising a dilution system, in which the air flow circulates at a generally constant flow rate, which emerges in a blower nozzle, and into which the substance is injected, of the type comprising a reservoir in which the substance is stored in liquid form, and a system for sampling a predetermined quantity of the substance, from the reservoir by means of a sampling gas, which emerges in the dilution system.

When a person wants to buy a perfume, it is desirable and advisable to smell this perfume first, in order to know in greater detail its fragrance and its characteristics. This is then called trying on the perfume, in the same manner as an item of clothing is tried on.

A first technique for trying on a perfume consists in applying a low dose of the perfume on the customer's own skin, usually at the wrist, and then sniffing the zone thus perfumed. The particular disadvantage of this technique is that it obliges the person to keep the sample of perfume on their skin.

Another technique of trying on a perfume consists in applying the perfume on the end of a more or less absorbent paper stick and sniffing the end of the stick thus perfumed.

These techniques of trying on perfume make it possible to have a good idea of the perfume's fragrance. However, the fragrance perceived by the person is mixed with the fragrance of the medium, which is only very rarely neutral. The perceived fragrance is therefore not the true fragrance of the perfume.

In addition, these techniques make it possible to recover only the portion of the perfume that was deposited on the medium.

Thus, the perfume particles that are the most volatile and that disperse rapidly in the air, forming what is called the "wash" of the perfume are recovered only to a small extent, or not at all.

These trying on techniques therefore give only a partial impression of what the perfume's true fragrance is.

According to other techniques of trying on a perfume, it is known to use a gas such as air or nitrogen, to form a medium of the perfume to be tested.

Specifically, in the "pure" state, this type of gaseous medium has no fragrance of its own capable of acting as a parasite on the perfume to be tested and the means for stripping such a gas medium of any parasitic fragrances that it may be carrying are relatively simple to implement.

Thus, the blowing of a gaseous flow filled with the perfume directly towards the face of a person allows that person to perceive the totality of the fragrance of the perfume to be tested, stripped of parasitic fragrances and much more realistically and close to the conditions in which the people surrounding a person wearing the perfume will effectively perceive that perfume.

Document U.S. Pat. No. 6,018,984 describes a device used to blow an air flow filled with a fragrance towards the face of a person.

This device comprises a first gas system in which the odour or the scent (fragrance or aroma) is mixed with a first air flow, and a second gas system in which this first "perfumed" air flow is aspirated by means of a tube forming a "venturi".

According to this document, the source of the fragrance may consist of a closed container in which a fragrant substance is stored, or else of a fragrance generator.

However, this document does not define the means for carrying the sampled fragrant substance from the source of fragrance to the zone for it to be mixed with the first air flow.

In addition, the device according to this document comprises a third gas system used to prevent a possible reflux of air into the first gas system.

Document U.S. Pat. No. 5,198,155 describes another device used to blow an air flow filled with a fragrance towards the face of a person.

The fragrance comes from a perfume reservoir which is traversed by a flow of nitrogen, such that the nitrogen is filled with a defined quantity of perfume.

The nitrogen thus filled with perfume is then injected into an air flow to be subsequently blown towards the face of the person.

Nitrogen is an odourless carrier gas. However, it is a gas that needs to be purified and stored in appropriate reservoirs, which involves a certain cost of use of the apparatus.

Furthermore, nitrogen cannot be breathed in without danger and it is therefore not suitable for "general public" usage due to the risk that it represents.

The aim of the invention is to propose a device for blowing air filled with a fragrant substance such as perfume, whose structure is simpler than the state of the art and which does not require the use of a particular gas for the sampling of a quantity of perfume.

For this purpose, the invention proposes a blowing device of the type previously described, characterized in that the sampling gas is air that is aspirated from a volume of ambient air.

According to other features of the device according to the invention:

- the sampling system comprises means for dividing the flow of sampling gas into a first fraction and a second fraction of sampling gas, such that the first fraction of the flow of sampling gas circulates in the reservoir while picking up the said determined quantity of substance, then is mixed with the second fraction of the flow of sampling gas which is used to regulate the pressure and/or the flow rate of sampling gas;
- the sampling system comprises means of regulating the pressure and/or the flow rate of the first and/or second fractions of the flow of sampling gas;
- the sampling system comprises a shut-off valve which is capable of cutting off the supply of sampling gas and whose opening and/or closing is controlled by an associated control system;
- the dilution system is mainly vertically oriented, such that the air flow circulates therein in an ascending motion;
- the dilution system comprises a bottom section forming a siphon, used to recover products of condensation, particularly water and/or the fragrant substance in the dilution system;
- the dilution system comprises a system for purifying the air flow.

A further aim of the invention is to propose an installation or demonstration array, used to blow individually and selectively several air flows filled with different perfumes, particularly for the purpose of selling perfumes in a shop fitted with such a perfume array.

For this purpose, the invention proposes a perfume installation or array in order to blow several air flows individually and selectively, each of which is filled with an associated perfume to be tested, characterized in that it comprises several blower devices according to any one of the preceding claims, which are aligned in a generally longitudinal and horizontal direction.

According to other features of the installation according to the invention:

the installation comprises several blowing devices that are aligned in a generally longitudinal and horizontal direction, and which all emerge in a common blower nozzle;

the installation comprises a single dilution system which is common to all the blower devices, and into which the sampling system of each of the blower devices emerges;

each blower nozzle is arranged at a height relative to the ground corresponding generally to the height of the face of a human being in a standing position in front of the installation;

each blower nozzle is mounted pivoting about a horizontal axis;

the installation comprises a first common source of air supplying all the dilution ducts of the said blower devices;

the installation comprises means for regulating, automatically and/or manually, the air flow rate supplied by the first source of air;

the installation comprises a device for causing a flushing air flow to circulate in each of the dilution systems;

the flushing air flow circulates in the dilution system in the opposite direction to the air flow;

the installation comprises a second common source of air supplying all the sampling ducts of the said blower devices;

the installation comprises a switch associated with each blower device, which controls the opening and/or closing of the associated shut-off valve and which is arranged beneath the associated nozzle.

Other features and advantages of the invention will appear on reading the following detailed description of the invention for the understanding of which reference will be made to the appended drawings in which.

To describe the invention, the vertical, longitudinal and transverse orientations will be used in a nonlimiting manner according to the V, L, T markings indicated on the figures.

In the following description, identical, similar or analogous elements will be identified by the same reference numbers.

Figure 1:
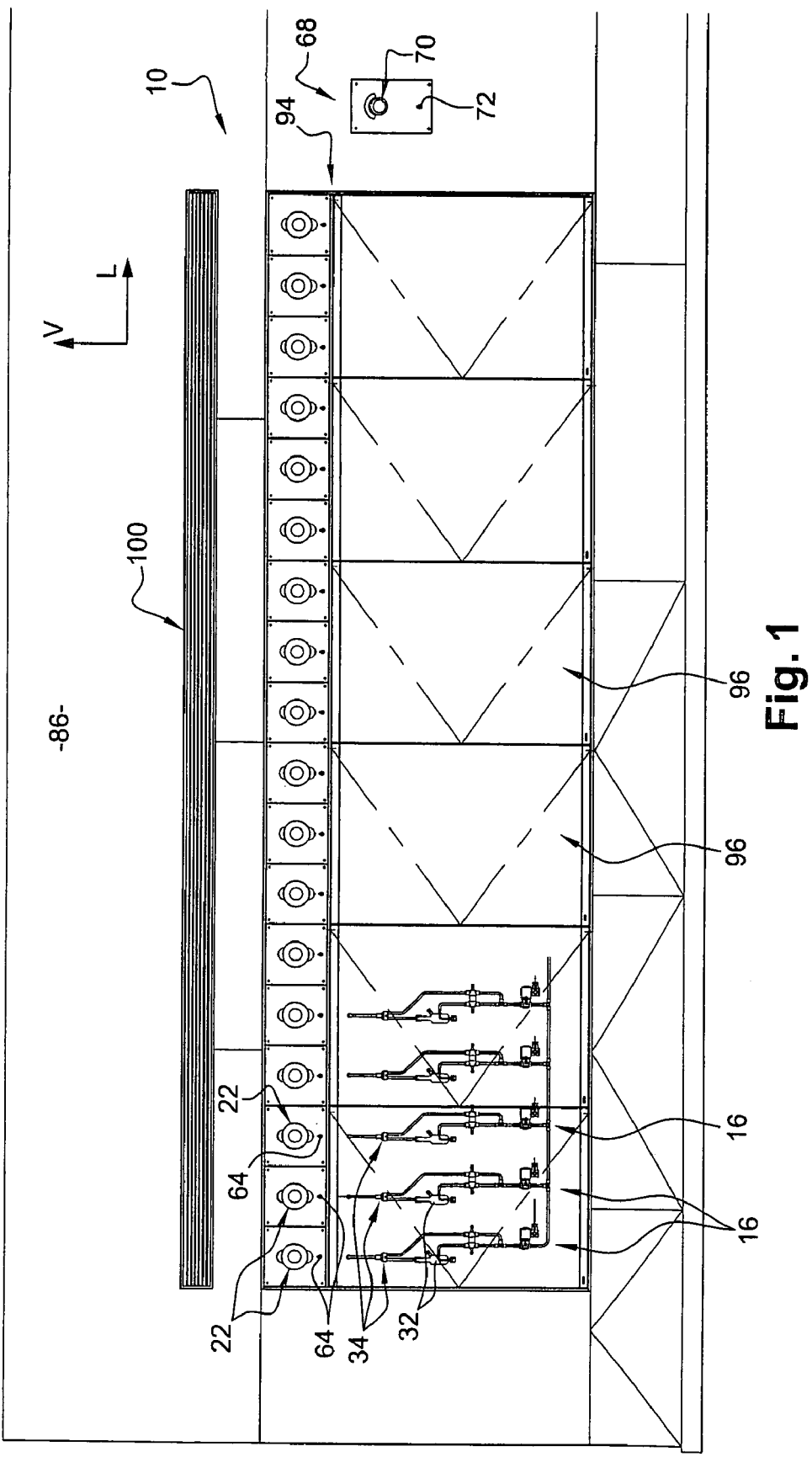
FIG. 1 is a schematic front view of the installation according to the invention, which comprises several blowing devices.
Figure 2:
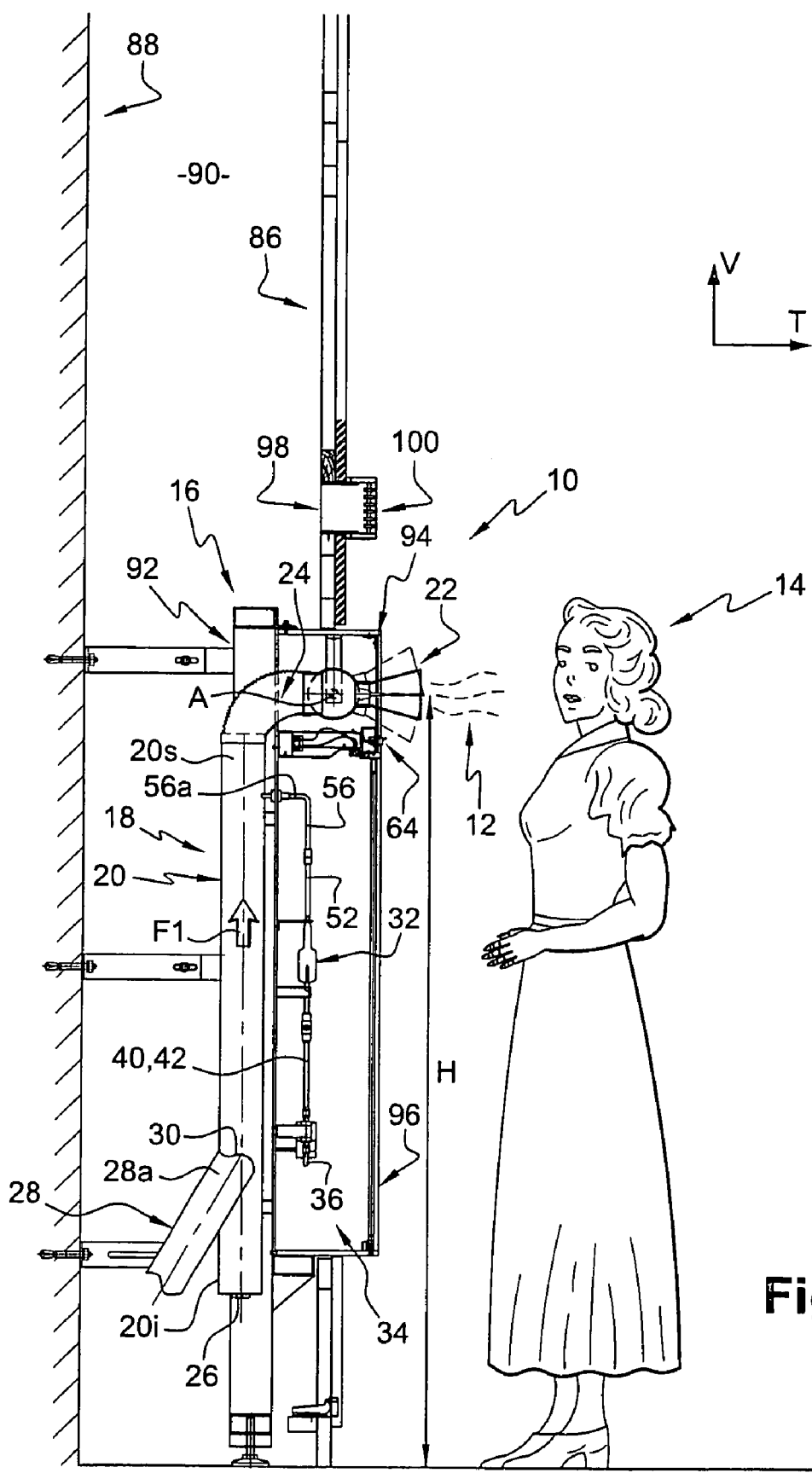
FIG. 2 is a view in section on a transverse vertical plane of the installation represented in FIG. 1.

FIGS. 1 and 2 show a perfume installation or array 10 which is for example intended to be used in a perfume shop and which is used to present to the customers various perfumes on sale so that they can try some of those perfumes in ideal conditions.

This array 10 is designed in order to blow individually and selectively several air flows 12, each of which is filled with an associated perfume, different from another perfume conveyed by another air flow 12.

To blow these various air flows 12 selectively, the array 10 comprises several blower devices 16, here eighteen in number, each of which can be used to blow independently a single air flow 12 filled with an associated perfume.

The blower devices 16 are all identical and they are laid out in the array 10 parallel with one another and they are aligned horizontally in a longitudinal direction.

In the following description, reference will be made in detail to a single blower device 16. Since the blower devices 16 of the array 10 are identical, it will be understood that this description applies in an identical manner to the other blower devices 16.

As can be seen in FIG. 2, a blower device 16 comprises a first air system 18, which will hereinafter be called the dilution system, in which the air flow 12 circulates and into which the perfume is injected.

The dilution system 18 comprises a main, vertically oriented tube 20, in which the air flow circulates in a vertical upward motion, as has been shown schematically by the arrow F1.

The top end 20s of the main tube 20 is connected, via a flexible pipe 24, to a nozzle 22 for blowing the air flow 12 towards the face of a person 14 wishing to try on the perfume, whose face is situated vertically and longitudinally substantially at the same level as the nozzle 22.

The bottom end 20i of the main tube 20 is blanked off in order to allow the recovery of various products resulting from the condensation of humidity and/or the perfume in the dilution system 18. The bottom end 20i of the main tube 20 thus forms a siphon and it comprises a plug 26 for emptying this siphon.

The dilution system 18 is supplied with air by means of a supply tube 28, of which only a downstream end section has been shown, and whose upstream end (considering the direction of Ihe flow of air in this duct) is connected to a first air source (not shown). The downstream end 28a of the supply tube 28 emerges in an additional orifice 30 of the main tube 20.

The first air source, which is preferably common to all the devices 16 of the installation, is for example a "fan" which draws in the ambient air in order to blow it into the installation.

As has been said hereinabove, a blower device 16 is used to blow an air flow 12 filled with a single determined perfume.

For this, a blower device 16 comprises a reservoir or individual container 32 in which the perfume, or a fragrant substance to be tested, is stored in liquid form.

To fill the air flow 12 with perfume, the blower device 16 comprises a second system 34 for sampling a quantity of perfume from the reservoir 32, this sampling system, 34 emerging in the dilution system 18 in order to inject a sampled quantity of perfume therein.

When the air flow 12 filled with perfume is blown, for the comfort of the person 14 trying on the perfume and to ensure a comparison of the perfumes in good conditions of repetitivity, it is desirable to have a substantially constant quantity of perfume injected into the air flow 12.

For this, the perfume is sampled from the reservoir 32 by means of a gas called a sampling gas.

This sampling gas must not have a particular odour risking distortion of the fragrance of the perfume, and it must not generate an excessive utilization cost, nor be harmful to the health of the customers.

Accordingly, and according to the invention, the sampling gas used in the sampling system 34 is air that is pumped from a volume of ambient air via a second air source (not shown).

This second air source is for example a compressor which draws in ambient air and injects it under pressure into the sampling system 34.

Each perfume has specific features concerning its fragrance. Thus, for example, based on equal quantities, one perfume may have a more intense fragrance than the fragrance of another perfume, at least as perceived as such by the people.

It is therefore necessary to regulate the quantity of perfume that is injected into the air flow 12.

Figure 3:
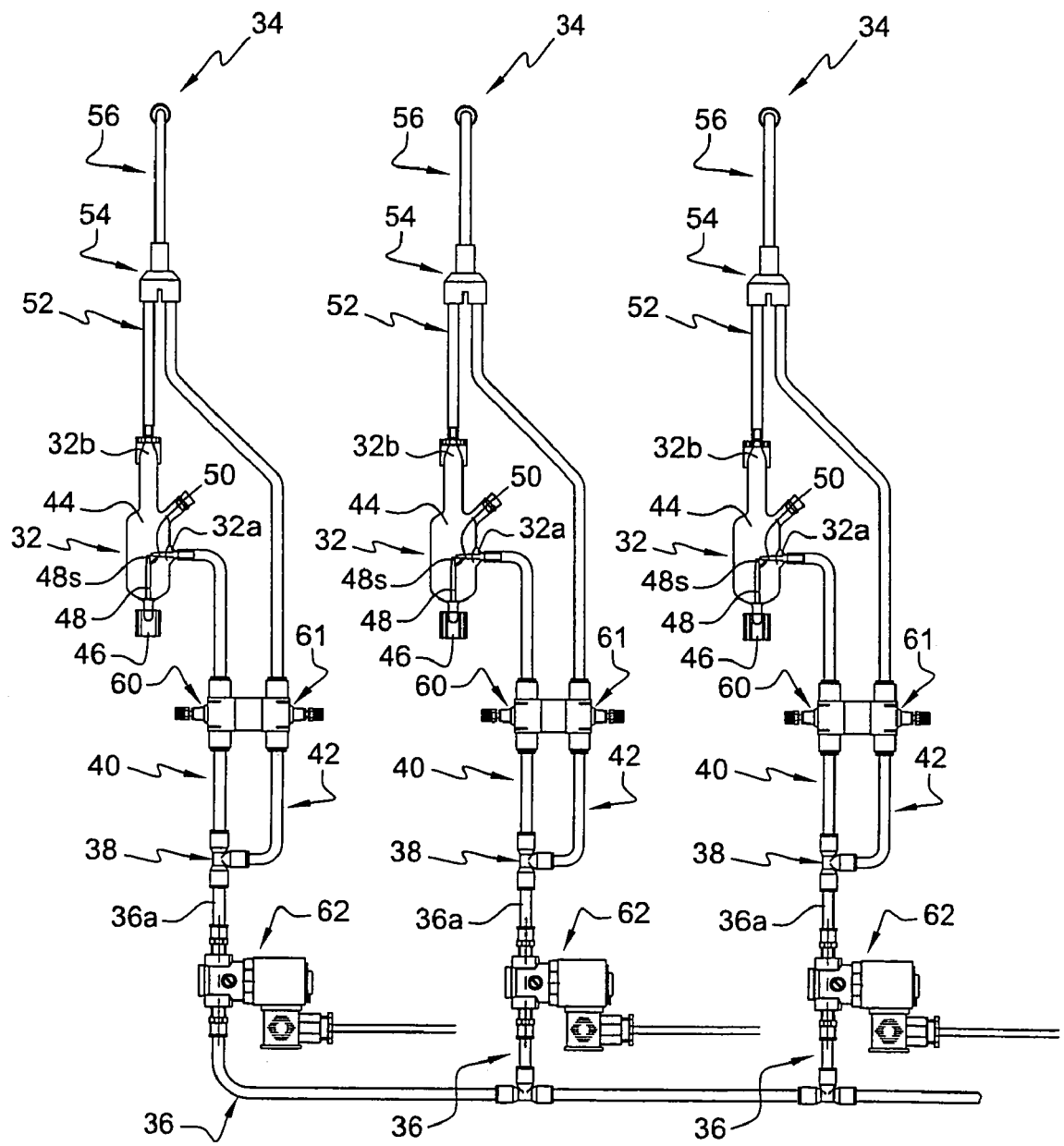
FIG. 3 is a detail on a larger scale of three of the sampling systems of the installation represented in FIG. 1.

For this, as can be seen in greater detail in FIG. 3, the sampling gas is divided into a first and a second fraction which respectively make it possible to carry out a regulation of the quantity of perfume sampled and a regulation of the sampling gas flow rate.

The sampling system 34 comprises an upstream tube 36 which is connected to the said second air source and in which all the sampling gas circulates.

The downstream end 36a of the upstream tube 36 is connected, via a divergent connector 38, to a sampling tube 40, in which the first fraction of the sampling gas circulates, and a secondary tube 42, in which the second fraction of the sampling gas circulates.

The sampling tube 40 is connected to an inlet orifice 32a of the reservoir 32 such that the first fraction of sampling gas circulates in the reservoir 32 and samples a determined quantity of the perfume.

In the example illustrated in the figures, a quantity of the perfume is sampled by causing the first fraction of sampling gas to circulate on the surface of the perfume in liquid form that is stored in the reservoir 32.

For this purpose, the reservoir 32 comprises a top chamber 44 in which the first fraction of the sampling gas circulates, a bottom reserve 46 in which the perfume is stored, and a capillary tube 48 which connects the reserve 46 to the chamber 44.

The capillary tube 48 is mainly vertically oriented and is emergent at its free top end 48s. The internal diameter of the capillary tube is determined so as to keep the perfume at a constant height inside the top chamber 44.

Finally, the reservoir comprises an internal nozzle 50 through which the first fraction of the sampling gas is blown directly onto the perfume present at the top end 48s of the capillary tube 48 in order to be filled with a quantity of perfume.

The first fraction of the sampling gas exits the internal nozzle 50 via an orifice of reduced section (not shown), which makes it possible to have a high speed of the first fraction of the sampling gas in the top chamber 44, in order to optimize the sampling of the perfume by the first fraction of sampling gas.

The means for sampling the perfume have been given here as an illustrative example, and it will be understood that the invention is not limited to this type of sampling means.

For example, as a variant not shown, it is possible to arrange for the first fraction of the sampling gas to circulate in the liquid perfume itself to be filled therein by contact with a quantity of this perfume.

The first fraction of the sampling gas that is filled with perfume leaves the reservoir 32 via an outlet orifice 32b to circulate in an outlet tube 52.

The outlet tube 52 is connected to the secondary tube 42 via a convergent connector 54, allowing the first fraction of the sampling gas filled with perfume and the second fraction of the sampling gas to mix together, such that all the sampling gas, previously fractioned, is filled with the sampled quantity of perfume.

Figure 4:
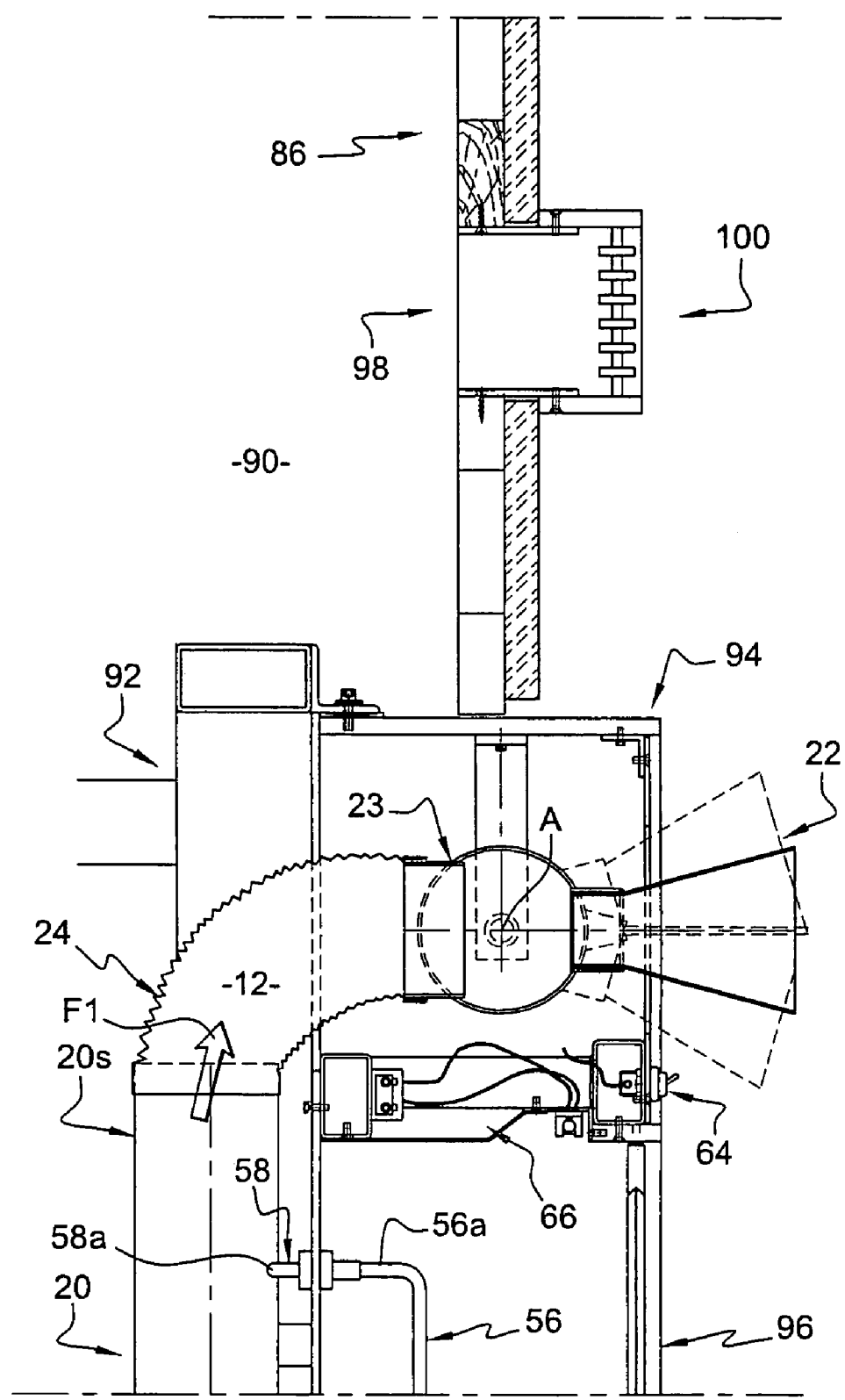
FIG. 4 is a detail on a larger scale of the downstream portion of the dilution system represented in FIG. 2.

The sampling gas thus filled with perfume then circulates in a downstream tube 56 whose upstream top end 56a emerges towards the internal volume of the main tube 20, as can be seen in FIGS. 2 and 4.

According to a preferred embodiment of the invention, the downstream end 56a of the downstream tube 56 is extended by an injector 58 which passes through the wall of the main tube 20, and which injects the sampling gas filled with perfume into the air flow 12 through its free end 58a.

The free end 58a of the injector 58 extends inside the main tube 20 and is conformed in such a manner as to inject the sampling gas filled with perfume while having an optimal diffusion of the sampling gas and of the perfume in the air flow 12.

As has been said hereinabove, it is necessary to regulate the quantity of perfume that is injected into the air flow 12.

For this purpose, as can be seen in FIG. 3, the sampling system 34 comprises means for regulating the pressure and/or the flow rate of each of the first and second fractions of the sampling gas flow.

According to a preferred embodiment of the invention, these regulation means comprise two flow rate regulators 60, 61 which can be regulated manually independently of one another and which are respectively associated with the sampling tube 40 and with the secondary tube 42.

The flow rate regulator 60 which is associated with the sampling tube 40 is used to regulate the pressure and the flow rate of the first fraction of the sampling gas and consequently the quantity of perfume that is sampled.

The flow rate regulator 61 that is associated with the secondary tube 42 is used to regulate the pressure and the flow rate of the second fraction of the sampling gas, thereby making it possible to regulate the pressure and the total flow rate of the sampling gas.

The two flow rate regulators 60, 61 are thus used to provide a complete range of possible adjustment values of the quantity of sampled perfume, of the pressure and of the flow rate of sampling gas.

The regulation of the pressure and of the flow rate of each of the first and second fractions of the sampling gas is carried out manually by an operator, mainly during the installation of a new perfume in the array 10.

This regulation is carried out so as to have an intensity of the perfume blown by the air flow 12 similar to that blown by the air flow of another blower device 16.

According to another aspect of the array 10, the quantity of perfume is injected into the air flow 12 only when the perfume is being tried on. During the rest of the time, the air flow 12 circulates in its neutral state, that is to say unperfumed, in the totality of the dilution system 18.

This is used to save perfume and prevents the volume of the room in which the air flow 12 is blown from being overfilled with the different fragrances of the perfumes.

Furthermore, the circulation of an air flow 12 unfilled with perfume in the dilution system 18 is used to clean the internal walls of the main tube 20, of the flexible pipe 24 and of the blower nozzle 22.

To turn on or off the injection of a quantity of perfume into the air flow 12, the sampling system 34 comprises a shut-off valve 62 that is arranged in the upstream tube 36.

When the valve 62 is in the closed position, the sampling gas cannot circulate in the sampling system 34, thus preventing the sampling of the perfume from the reservoir 32. When the valve 62 is in the open position, the sampling gas circulates in the sampling system 34 to sample the perfume and inject it into the air flow, as previously described.

The opening or closing of the valve 62 is controlled by means of a control button 64 which is connected to the valve 62 by means of an electronic control device 66 that has been shown in particular in FIG. 4.

The electronic control device 66 is designed dependent on the type of control of the valve 62.

Specifically, an action on the control button 64 causes the valve 62 to open. However, closure of the valve 62 may be controlled differently.

According to a first embodiment of the electronic control device 66, closure of the valve 62 is controlled when the control button 64 is released. This means that the control button 64 has to be kept actuated to obtain an injection of perfume into the air flow 12.

According to a second embodiment of the electronic control device 66, closure of the valve 62 is controlled when the control button 64 is actuated again.

Finally, according to a third embodiment of the electronic control device 66, closure of the valve 62 is automatic and timed after a predefined period of time has elapsed. The electronic control device 66 then comprises a time delay system.

It will be understood that these embodiments of the control device 66 are given as illustrative examples and that the invention may also apply to other types of control devices 66.

According to a variant embodiment of the control of the valve 62, the control button 64 is directly connected to the valve 62, electrically or pneumatically, such that when the control button 64 is actuated the valve 62 opens, and when the control button 64 is released, the valve 62 closes.

As can be seen in the figures, the control button 64 is arranged close to the blower nozzle 22 of the associated blower device 16, and preferably beneath the blower nozzle 22.

Thanks to this arrangement of the control button 64, it is not possible to make an error relating to the valve 62 whose opening is controlled.

To try on one of the various perfumes presented, as can be seen in FIG. 2, the person 14 places their face in the air flow 12 conveying the perfume in question and breathes in the air flow 12 in order to smell the fragrance of the perfume that it conveys.

To compare different perfumes with one another, the person 14 moves along the array 10 placing their face in the air flow of the blower devices 16 corresponding to these perfumes.

In order to make this trying on as comfortable as possible, the various nozzles 22 are all placed such that the person 14 does not continually have to stoop or stretch when they want to try a different perfume.

This is why, according to the invention, the blower nozzles 22 are all arranged at a height "H" corresponding to the height of the face of the person 14 when in a standing position.

Since human beings vary in size, it is not possible to have a single height "H" of the nozzles 22 making it possible to blow an air flow 12 at the face of just any person.

For this purpose, according to the invention, the nozzles 22 are mounted pivoting about a horizontal axis A which here is generally longitudinally oriented.

It is then possible to tilt the nozzles 22 up or down, as has been shown in dashed lines in FIG. 4, in order to adapt the direction of travel of the air flow to suit the size of the person 14.

The blower nozzle 22 comprises a rear portion 23 which is of cylindrical shape, coaxial with the axis A of articulation of the blower nozzle 22, and which is connected to the flexible pipe 24 so as to allow a circulation of the air flow 22 without leaks, irrespective of the angular position of the blower nozzle 22 about the longitudinal axis A.

As has been said hereinbefore, the dilution systems 18 of all the blower devices 16 are supplied by a first common source of air.

This common source of air makes it possible to have one and the same flow rate of air coming out of all the nozzles 22.

To ensure the neutrality of the air delivered by the first source of air, an air purification device (not shown) is arranged upstream or downstream of the first air source, and it is designed so as to remove from the aspirated air all polluting elements that may adversely affect the comfort for the person 14 when trying on the perfume.

Among the components of the purification device, mention is made in particular of a filter used to stop dust and pollens present in the air, an odour filter, such as for example an active charcoal filter, and an air dehumidifier.

According to yet another aspect of the invention, the air flow delivered by the first source of air is adjustable.

It is then possible to have a first air flow which is delivered during the period of opening of the shop and a second air flow delivered outside shop opening hours.

The first flow is determined such that the air flow 12 in all the blower devices 16 is sufficient to be blown at the face of the person 14, while not detracting from the comfort of trying on the perfume.

The second air flow is greater than the first air flow. This is used to circulate a larger quantity of air in the tubes 20 of the dilution system 18, and makes it possible to clean these tubes by removing any trace of perfume that may have been deposited on the internal walls of the various tubes 20.

The first source of air is controlled by an electronic control device 68, that has been shown in FIG. 1, and that comprises a switch 70 with at least two positions, each corresponding to a value of the air flow delivered by the first source of air.

As a variant embodiment of the invention, the switch 70 is replaced by a rheostat which is used to modify the air flow continuously according to the operating circumstances of the installation.

According to yet another variant embodiment of the invention, the switch 70 is replaced by a programmable electronic device, which is used to dispense with the intervention of a person to modify the air flow.

Finally, the electronic control device 68 comprises a main switch 72 making it possible to switch on or switch off all the sampling systems 34, that is to say the second source of air, and the valves 62.

Figure 5:
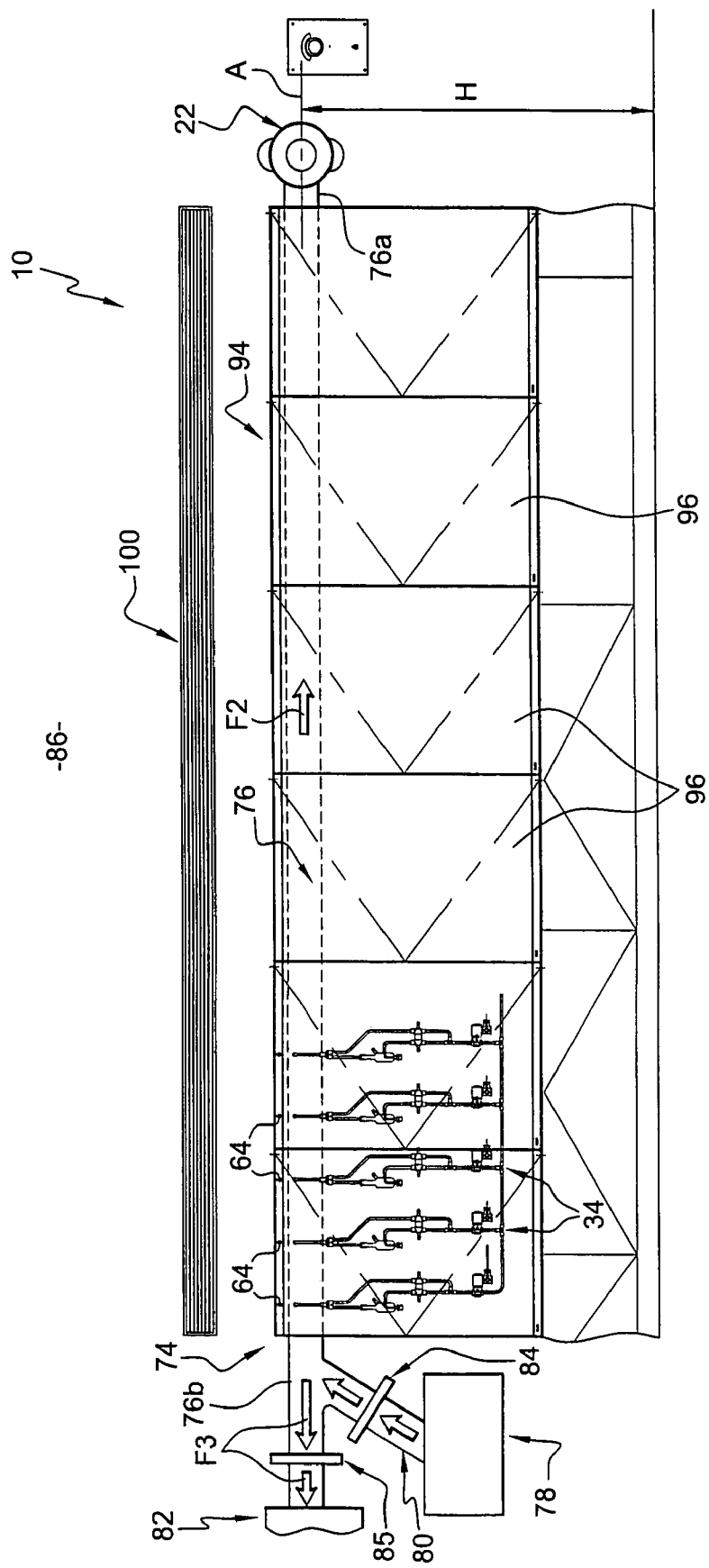
FIG. 5 is a view similar to that of FIG. 1, representing a variant embodiment, which comprises a single dilution system emerging into a single blower nozzle.

FIG. 5 shows a variant embodiment of the array 10, which comprises a single dilution system 74 into which each of the perfumes is injected in a distinct and isolated manner.

This single dilution system 74 comprises a main tube 76 which extends horizontally and which is mainly longitudinally oriented, and a first end 76a of which emerges in a single blower nozzle 22, which here is arranged at the right end of the array 10.

The single dilution system 74 is supplied with air forming the air flow 12 by the first source of air 78 at its second end 76b, by means of a supply tube 80.

The first source of air 78 is therefore arranged at the other end of the array 10, relative to the blower nozzle 22, that is to say here the left end of the array 10.

Thus, in the embodiment shown in FIG. 5, the air flow 12 which circulates in the main tube 76 of the single dilution system 74 flows horizontally from left to right as shown by the arrow F2.

All the sampling systems 34 of the blower devices 16 emerge, via their respective downstream tube 56, directly into the main tube 76 of the single dilution system 74.

According to this variant embodiment of the array 10, since all the blower devices 16 are connected to a single blower nozzle 22, the person 14 who wishes to try on perfumes no longer has to move from one blower nozzle 22 to the other when trying on the various perfumes. This provides the person with a particularly advantageous additional degree of convenience.

According to a first aspect of this variant embodiment of the array 10, the blower nozzle 22 is here also arranged at a height H corresponding to the height of the face of the person 14 and it is mounted pivoting about the longitudinal axis A.

However, according to another aspect of this variant, the person 14 is not obliged to remain standing or to move. Consequently, according to this other aspect of the variant, the blower nozzle 22 is arranged at a lower height H, for example the height of the face of the person 14 when that person is in the seated position.

The perfume to be injected into the single dilution system 74 is then selected by means of an operator, such as the shop assistant, who selectively actuates one of the control buttons 64 that are respectively associated with the blower devices 16.

The control buttons 64 may also be grouped together in a control panel.

Also shown in FIG. 5 is a variant embodiment of the means for "cleaning" the single dilution system 74.

According to this variant, the second left end 76b of the main tube 76 is also connected to an extractor 82, which consists for example of a fan similar to the fan that forms the first source of air 78.

To clean the single dilution system 74, the extractor 82 is suitable for supplying a cleaning air flow which flows in the single dilution system 74 in the direction contrary to the direction of circulation of the air flow 12 supplied by the first source of air 78, that is to say here from right to left, as shown by the arrow F3.

To prevent this cleaning air flow from being disrupted by the air flow 12, and conversely, to prevent the air flow 12 from being disrupted by the cleaning air flow, the second end 76b and the supply tube 80 each comprise an electrovalve 84, 85 which is controlled by the switch 70 of the control panel 68, so that only one electrovalve 84 or 85 is open at a time.

Thus, here, the electrovalve 84 associated with the first source of air 78 is open when perfume is being blown and the electrovalve 85 associated with the extractor 82 is open when the single dilution system 74 is being cleaned.

The array 10 is arranged through a vertical longitudinal partition 86 of the shop.

The partition 86 is situated at a relatively short distance from a parallel wall 88 of the shop, so as to define a space 90 in which at least the dilution system 18 of each blower device 16 is arranged.

A supporting structure 92 is also arranged in this space 90, and it supports the main tubes 20 and the supply tubes 28 of the blower devices 16.

As can be seen in FIG. 4, the partition 86 is traversed by a cabinet 94 in which the sampling systems 34 and blower nozzles 22 are arranged, and which comprises movable external panels 96 that can be used to hide the sampling systems 34.

According to a preferred embodiment of the arrangement of the array 10, the second source of air pumps the air supplying the sampling systems 34 into the space 90 situated between the partition 86 and the wall 88, which, amongst other things, reduces the sound distractions produced by this second source of air.

To ensure a correct renewal of the air present in this space 90, the partition 86 comprises an opening 98 making the space 90 communicate with the rest of the volume inside the shop and which is blanked off by a protective grille 100.

It will be understood that the vertical or longitudinal orientations of the various dilution systems 18, and sampling systems 34 are given as an illustration of the example shown in the figures, and that these systems may be oriented differently without departing from the field of the invention.

Thus, as a variant of the invention, the dilution systems 18 may all be horizontal, the single dilution system 74 may be vertical, the sampling systems 34 may also be horizontal and longitudinally or transversely oriented.

The same applies to the directions of circulation of the various gas flows in the various ducts which may be inverted relative to the directions of circulation described, in relation with the various orientations of the dilution systems 18 and/or sampling systems 34.

The installation of an array according to the invention can be used to blow an air flow, into which a predefined quantity of a perfume is injected, onto the face of a person, to allow that person to smell the fragrance of the perfume in all its aspects.

This installation uses air drawn from a volume of ambient air, thereby ensuring the safety of the person breathing in that air flow.

Finally, this installation allows the person to try on the perfume in particularly comfortable conditions.

The invention claimed is:

1. Device (16) for blowing an air flow (12) filled with a fragrant substance, comprising:
   a dilution system (18), in which the air flow (12) circulates at a generally constant rate, which emerges into a blower nozzle (22) and into which the substance is injected,
   a reservoir (32) in which the substance is stored in liquid form, and
   a system for sampling (34) a predetermined quantity of the substance, from the reservoir (32) by means of a sampling gas consisting of the air aspirated from a volume of ambient air, which emerges into the dilution system (18), wherein,
   the sampling system (34) comprises means for dividing the flow of sampling gas into a first fraction and a second fraction of sampling gas, such that the first fraction of the flow of sampling gas circulates in the reservoir (32) picking up the said determined quantity of substance, then is mixed with the second fraction of the flow of sampling gas which is used to regulate the pressure and/or the flow rate of sampling gas, and
   the sampling system (34) comprises a shut-off valve (62) which is capable of cutting off the supply of sampling gas and whose opening and/or closing is controlled by an associated control system (64, 66).

2. Blower device (16) according to claim 1, characterized in that the sampling system comprises means (60) of regulating the pressure and/or the flow rate of the first and/or second fractions of the flow of sampling gas.

3. Blower device (16) according to claim 1, characterized in that the dilution system (18) is mainly vertically oriented, such that the air flow (12) circulates therein in an ascending motion.

4. Blower device (16) according to claim 1, characterized in that the dilution system (18) comprises a bottom section (20i) forming a siphon, used to recover products of condensation, particularly water and/or the fragrant substance in the dilution system (18).

5. Blower device (16) according to claim 1, characterized in that the dilution system (18) comprises a system for purifying the air flow (12).

6. Installation (10) for selectively and individually blowing several air flows (12) each of which is filled with an associated perfume to be tested, characterized in that the installation comprises several blower devices (16) according to claim 1, which are aligned in a generally longitudinal and horizontal direction.

7. Installation (10) for blowing an air flow (12) filled with a single fragrant substance selected from a defined set of distinct fragrant substances, characterized in that the installation comprises several blower devices (16) according to claim 1, which are aligned in a generally longitudinal and horizontal direction, and which all emerge in a common blower nozzle (22).

8. Installation (10) according to claim 7, characterized in that the installation comprises a single dilution system (74) which is common to all the blower devices (16), and into which the sampling system (34) of each of the blower devices (16) emerges.

9. Installation (10) according to claim 6, characterized in that each blower nozzle (22) is arranged at a height (H) relative to the ground corresponding generally to the height of the face of a human being (14) in a standing position in front of the installation (10).

10. Installation (10) according to claim 9, characterized in that each blower nozzle (22) is mounted pivoting about a horizontal axis (A).

11. Installation (10) according to claim 6, characterized in that the installation comprises a first common source of air supplying all the dilution ducts (18) of the said blower devices (16).

12. Installation (10) according to claim 11, characterized in that the installation comprises means (70) for regulating, automatically and/or manually, the air flow rate supplied by the first source of air.

13. Installation (10) according to claim 6, characterized in that the installation comprises a device for causing a flushing air flow to circulate in each of the dilution systems (18).

14. Installation (10) according to claim 13, characterized in that the flushing air flow (12) circulates in the dilution system (18) in the opposite direction to the air flow (12).

15. Installation (10) according to claim 6, characterized in that the installation comprises a second common source of air supplying all the sampling ducts (34) of the said blower devices (16).

16. Installation (10) according to claim 6, characterized in that the installation comprises a switch (34) associated with each blower device (16), which controls the opening and/or closing of the associated shut-off valve (62) and which is arranged beneath the associated nozzle (22).

17. Device of claim 1, wherein the fragrant substance is a perfume.

18. Device (16) for blowing an air flow (12) filled with a fragrant substance, comprising:
a dilution system (18), in which the air flow (12) circulates at a generally constant rate, which emerges into a blower nozzle (22) and into which the substance is injected,
a reservoir (32) in which the substance is stored in liquid form, and
a system for sampling (34) a predetermined quantity of the substance, from the reservoir (32) by means of a sampling gas consisting of the air aspirated from a volume of ambient air, which emerges into the dilution system (18), wherein,
the sampling system (34) comprises means for dividing the flow of sampling gas into a first fraction and a second fraction of sampling gas, such that the first fraction of the flow of sampling gas circulates in the reservoir (32) picking up the said determined quantity of substance, then is mixed with the second fraction of the flow of sampling gas which is used to regulate the pressure and/or the flow rate of sampling gas, and
the dilution system (18) is mainly vertically oriented, such that the air flow (12) circulates therein in an ascending motion.

19. Device (16) for blowing an air flow (12) filled with a fragrant substance, comprising:
a dilution system (18), in which the air flow (12) circulates at a generally constant rate, which emerges into a blower nozzle (22) and into which the substance is injected,
a reservoir (32) in which the substance is stored in liquid form, and
a system for sampling (34) a predetermined quantity of the substance, from the reservoir (32) by means of a sampling gas consisting of the air aspirated from a volume of ambient air, which emerges into the dilution system (18), wherein,
the sampling system (34) comprises means for dividing the flow of sampling gas into a first fraction and a second fraction of sampling gas, such that the first fraction of the flow of sampling gas circulates in the reservoir (32) picking up the said determined quantity of substance, then is mixed with the second fraction of the flow of sampling gas which is used to regulate the pressure and/or the flow rate of sampling gas, and
the dilution system (18) comprises a bottom section (20i) forming a siphon, used to recover products of condensation, including water and the fragrant substance, in the dilution system (18).

* * * * *